(12) United States Patent
Paik et al.

(10) Patent No.: US 8,961,499 B2
(45) Date of Patent: Feb. 24, 2015

(54) SURGICAL INSTRUMENT

(75) Inventors: Jamie Paik, Lausanne (CH); Guillaume Morel, Bry sur Marne (FR); Clément Vidal, Grenoble (FR); Patrick Henri, Bois-Colombes (FR); Hervé Collet, Chatenay (FR)

(73) Assignees: Universite Pierre et Marie Curie (Paris 6), Paris (FR); Endocontrol, La Tronche (FR); Centre National de la Recherche Scientifique (CNRS), Paris (FR)

( * ) Notice: Subject to any disclaimer, the term of this patent is extended or adjusted under 35 U.S.C. 154(b) by 578 days.

(21) Appl. No.: 13/260,909

(22) PCT Filed: Apr. 2, 2010

(86) PCT No.: PCT/EP2010/054471
§ 371 (c)(1),
(2), (4) Date: Sep. 28, 2011

(87) PCT Pub. No.: WO2010/112609
PCT Pub. Date: Oct. 7, 2010

(65) Prior Publication Data
US 2012/0022554 A1    Jan. 26, 2012

(30) Foreign Application Priority Data
Apr. 3, 2009   (FR) ..................... 09 52186

(51) Int. Cl.
*A61B 17/00*   (2006.01)
*A61B 19/00*   (2006.01)
(Continued)

(52) U.S. Cl.
CPC ....... *A61B 17/29* (2013.01); *A61B 2017/00314* (2013.01); *A61B 2017/00323* (2013.01);
(Continued)

(58) Field of Classification Search
CPC ................... A61B 2017/0069; A61B 17/2804; A61B 17/29
See application file for complete search history.

(56) References Cited

U.S. PATENT DOCUMENTS

| 726,458 A | 4/1903 | Purper et al. |
| 4,294,345 A | 10/1981 | Stauber et al. |

(Continued)

FOREIGN PATENT DOCUMENTS

| DE | 42 43 715 A1 | 7/1994 |
| JP | 7-410 | 1/1995 |

(Continued)

OTHER PUBLICATIONS

Non-Final Office Action dated Feb. 22, 2013 for U.S. Appl. No. 13/260,910, 15 pages.

*Primary Examiner* — Elizabeth Houston
*Assistant Examiner* — Todd J Scherbel
(74) *Attorney, Agent, or Firm* — Blakely Sokoloff Taylor & Zafman (57) ABSTRACT

A surgical instrument having an elongated arm and a distal end mounted with a pivot joint on the elongated arm. A drive shaft substantially coaxial with the elongated arm forms a universal joint facing the pivot joint. A distal tool is securely fastened on the drive shaft and rotatively mounted on and in the extension of the distal end of the elongated arm, such that the distal tool has two rotational degree of freedom, distinct and independent of each other, one being around an axis substantially perpendicular to the longitudinal axis of the elongated arm and the other being around an axis substantially collinear to an own axis of the distal tool. The elongated arm includes a plurality of linking elements mounted in series to form the pivot joint. The universal joint is a Cardan joint.

19 Claims, 9 Drawing Sheets

(51) Int. Cl.
*A61B 1/00* (2006.01)
*A61B 17/29* (2006.01)

(52) U.S. Cl.
CPC . *A61B2017/0069* (2013.01); *A61B 2017/2902* (2013.01); *A61B 2017/2927* (2013.01); *A61B 2017/2929* (2013.01)
USPC ................ 606/1; 606/130; 606/167; 606/205

(56) References Cited

U.S. PATENT DOCUMENTS

| | | | |
|---|---|---|---|
| 5,448,989 | A | 9/1995 | Heckele |
| 5,549,637 | A | 8/1996 | Crainich |
| 5,624,398 | A | 4/1997 | Smith et al. |
| 5,643,294 | A | 7/1997 | Tovey et al. |
| 5,749,828 | A | 5/1998 | Solomon et al. |
| 5,755,731 | A | 5/1998 | Grinberg |
| 6,743,239 | B1 | 6/2004 | Kuehn et al. |
| 6,840,951 | B2 | 1/2005 | de la Torre et al. |
| 6,875,170 | B2 | 4/2005 | Francois et al. |
| 6,913,613 | B2 | 7/2005 | Schwarz et al. |
| 7,241,288 | B2 | 7/2007 | Braun |
| 7,316,681 | B2 | 1/2008 | Madhani et al. |
| 7,338,513 | B2 | 3/2008 | Lee et al. |
| 7,398,707 | B2 | 7/2008 | Morley et al. |
| 8,398,619 | B2 * | 3/2013 | Doyle et al. ........................ 606/1 |
| 8,845,622 | B2 * | 9/2014 | Paik et al. ........................ 606/1 |
| 2001/0031983 | A1 | 10/2001 | Brock et al. |
| 2004/0225323 | A1 | 11/2004 | Nagase et al. |
| 2004/0260335 | A1 | 12/2004 | Braun |
| 2005/0033357 | A1 | 2/2005 | Braun |
| 2007/0043259 | A1 | 2/2007 | Jaffe et al. |
| 2007/0219581 | A1 | 9/2007 | Dohi et al. |
| 2008/0046000 | A1 | 2/2008 | Lee et al. |
| 2008/0147113 | A1 | 6/2008 | Nobis et al. |
| 2008/0228196 | A1 | 9/2008 | Wang et al. |
| 2008/0294191 | A1 | 11/2008 | Lee |
| 2012/0022554 | A1 | 1/2012 | Paik et al. |
| 2012/0083770 | A1 * | 4/2012 | Paik et al. ........................ 606/1 |

FOREIGN PATENT DOCUMENTS

| | | |
|---|---|---|
| JP | 08-164141 | 6/1996 |
| JP | 9-182737 | 7/1997 |
| JP | 2004-154164 | 6/2004 |
| JP | 2004-164164 | 6/2004 |
| JP | 2004-329624 | 11/2004 |
| JP | 2009-8223 | 1/2009 |
| WO | WO 93/00048 | 1/1993 |
| WO | WO 02/07611 | 1/2002 |
| WO | WO 2007/139734 | 12/2007 |

* cited by examiner

SURGICAL INSTRUMENT

This is a non-provisional application claiming the benefit of International Application Number PCT/EP2010/054471, filed Apr. 2, 2010.

FIELD OF THE INVENTION

The invention relates to a surgical instrument designed for endoscopic or laparoscopic surgical operations.

TECHNICAL BACKGROUND

Within the scope of minimally-invasive surgery, such as endoscopic or laparoscopic surgery, access to the operating site is made via small incisions in the body of the patient (such as the abdomen or thorax), in which the practitioner places a canula formed by a tube whereof the diameter varies from 3 to 15 mm, via which the practitioner can insert into the body of the patient either an endoscope for obtaining a video image on a monitor, or long and fine instruments for performing a procedure at the operating site.

The majority of existing instruments is constituted by a fine (typically around 5 mm in diameter) and rigid elongated body (typically around 30 cm long). The proximal end of the instrument comprises a grip handle for the practitioner and the distal end of the instrument is often fitted with a forceps or scissors, optionally capable of transmitting electric current for cutting (monopolar or bipolar).

The main advantage of laparoscopic surgery is the minimum incisions. However, the main limitation is the decrease in dexterity associated with a remote access by long instruments. Indeed, when the instrument is rigid, its passage via a fixed incision point is a planar kinematic constraint which limits the number of degrees of freedom (DoF) to four: three movements of rotation about the point of incision and a penetration translation movement of the instrument. In particular, with conventional laparoscopic rigid instruments, it is impossible to bend the distal end of the instrument to orient the forceps optimally relative to the practitioner. This is a major application limitation of laparoscopic surgical tools for surgical procedures.

This has led to the development of novel instruments comprising a distal part exhibiting mobility relative to the principal body of the instrument. For example, for suturing exercise, the surgeon utilises a curved needle. When he carries out this exercise in optimal conditions, the surgeon:
  1. grasps the needle such that the plane of the needle is perpendicular to the axis of the forceps;
  2. places the plane of the needle perpendicularly to the edges to be sutured;
  3. turns the needle according to an axis perpendicular to its plane to insert into the tissue to be sutured, Therefore, to make a suture in favourable conditions, there must be provision for placing the axis of the instrument substantially parallel to the edges to be sutured and turning the forceps about its axis. During some interventions, positioning the points of incision relative to the operating site is such that it is not possible to align the axis of the forceps with the edges to be sutured when using rigid instruments, substantially complicating making the suture. This is why instruments have been developed which orient the axis of the forceps relative to the principal axis of insertion of the instrument in the body, due to distal mobility.

It should be noted that the final rotation movement of the forceps on itself (intrinsic rotation of the forceps), which controls penetration of the needle, must be made with a high precision and a maximal stability of the direction of the axis of the forceps while applying sufficient force to perforate tissue.

Instruments having a distal mobility are described in documents U.S. Pat. No. 7,338,513, U.S. Pat. No. 7,316,681, U.S. Pat. No. 7,398,707 and US 20080228196.

The instruments described in these documents are such that the axis of the forceps can be oriented relative to the principal axis of insertion of the instrument according to rotation made about any axis perpendicular to the principal axis of insertion. This is done either by a system with flexible sleeve and cables (document U.S. Pat. No. 7,338,513) or by using two perpendicular pivot joints (document U.S. Pat. No. 7,398,707). In both cases, two rotational degrees of freedom between the principal axis of insertion and the axis of the forceps result from the mechanism used. By using the intrinsic rotation of the axis of insertion, freed by the canula placed at the level of the point of insertion, it is therefore possible to combine three rotations and produce all preferred orientations of the forceps. However, to produce the movement described previously for a suturing exercise, that is, intrinsic rotation of the forceps, in general a complex combination of these three movements and their synchronisation is required at the level of their actuation, making carrying out the exercise very complex. With a design having sleeves and cables (document U.S. Pat. No. 7,338,513), the rigidity of the assembly is insufficient and the axis of the forceps can remain stable and turn on itself when forces are exerted, only with difficulty. With a system having pivots and three combined rotations, a complex robotic system is required to perform synchronisation of movements (document U.S. Pat. No. 7,398,707).

Other documents describe instruments for which movement of the forceps occurs without resulting from a combination of three rotations. In the document U.S. Pat. No. 7,241,288, the forceps is operated by a system of gears and can be either bent (orientation of the axis of the forceps), or oriented about its axis (intrinsic rotation). However, for controlling one or the other of the movements, a mechanical clutch must be used. The movements are therefore not controlled directly by independent proximal movements.

The instruments described in the document U.S. Pat. No. 6,913,613 comprise a flexible rod, though rigid to torsion according to its axis, enabling orienting a distal forceps according to its axis and a rigid control rod of the inclination of this forceps relative to an axis of the tool. The two rods extend in a tube. The instrument is difficult to make and is complex.

An aim of the invention is to provide a surgical instrument being simple in use, and which addresses at least one of the limitations and drawbacks mentioned above.

SUMMARY OF THE INVENTION

To this end, there is provided a surgical instrument comprising:
  an elongated arm according to a longitudinal axis and having a distal end mounted with a pivot joint on the elongated arm according to an axis substantially orthogonal to the longitudinal axis;
  a drive shaft substantially coaxial with the elongated arm comprising means forming a universal joint facing the pivot joint; and,
  a distal tool securely fastened on the drive shaft and rotatively mounted on and in the extension of the distal end of the elongated arm, such that the distal tool has two rotational degree of freedom, distinct and independent of each other, one being around an axis substantially perpendicular to the longitudinal axis of the elongated arm and the other being around an axis substantially collinear to an own axis of the distal tool;

characterised in that the elongated arm comprises a plurality of linking elements mounted in series to form the pivot joint and in that the means forming a universal joint comprise a Cardan joint.

It should here be noted that in conventional terms, a universal joint is a kinematic joint used for connecting two shafts and adapted for transmission of the rotational movement of one shaft to another, whatever the angular position of one shaft relative to the other is. There exists several types of universal joint, the Cardan joint being one specific example thereof. Basically, a Cardan joint consists of a mechanical linking system comprising two end elements mounted on either side of a central element, wherein each end element is mounted in a pivot joint with the central element, the axis of two pivot joints in the central element being perpendicular.

According to the proposed invention, the enabled direct transmission produces an infinite rotation of the forceps about its own axis, without having to modify the position of the axis of the forceps, or reconfiguring movements or using a clutch system. All rotations are maintained and/or actuated independently. Further, all rotations may be actuated simultaneously if required. It is not necessary to reverse or cancel rotation to describe any movement on the other rotation. Because of this, distal movements are selected optimally to ensure simple control of the instrument while a suturing exercise for example is carried out. Using a Cardan joint as universal joint in combination with the linking elements mounted in series greatly simplifies manufacturing of the instrument.

Advantageously, though optionally, the surgical instrument has at least one of the following characteristic, taken individually or in combination:

two adjacent linking elements are mounted relative to one another with a limited pivot joint.

each linking element is a hollow cylindrical element comprising two lugs extending towards the adjacent linking element, said lugs being opposite one another to define the limited pivot joint.

the means forming a universal joint comprise as many Cardan joints as limited pivot joints between the linking elements mounted in series.

the means forming a universal joint comprise at least two Cardan joints and in that the elongated arm comprises at least three linking elements mounted in series to form the pivot joint with two limited pivot joints.

each Cardan joint is facing one of the limited pivot joints formed by the linking elements mounted in series, each Cardan joint comprising two pivot axes intersecting with a pivot axis of the corresponding limited pivot joint.

the Cardan joint comprises two end elements mounted on either side of a central element, each end element being mounted with a pivot joint on the central element according to perpendicular pivot axes, wherein the pivot joints between each of the end elements and the central element are made by a guided sliding of the corresponding contact surfaces.

the central element has the form of a sphere with two grooves hollowed in two perpendicular diametrical planes, and in that the end elements have ends with a concave surface formed to be able to slide on the sphere.

the concave surfaces of the end elements further comprise a ridge in projection with a shape complementary to the grooves of the sphere, such that the ridges in projection serve as guide rail for sliding of the end elements on the central element.

the end elements and the central element of the Cardan joint comprise a through-hole along the longitudinal axis, one or more cables extending in the elongated arm via the through-hole.

an actuating cable of the distal tool extends in the elongated arm via the through-hole, said actuating cable being surrounded by a sheath.

the drive shaft is further slidingly mounted according to a translation relative to the elongated arm along the longitudinal axis, the means forming a universal joint comprising two Cardan joints mounted in series.

the elongated arm is hollow and at least partially encloses the drive shaft.

the surgical instrument further comprises a handle and a transmission system, wherein the handle is connected to the proximal end of the elongated arm, the movements according to the two degrees of freedom being connected by the transmission system to two independent movements produced at the handle.

the surgical instrument is arranged such that the amplitude of rotation of the tool about its own axis is not structurally limited by the transmission system.

BRIEF DESCRIPTION OF THE DRAWINGS

Other features and advantages of the invention will become clear from the following description which is only given for illustrative purposes and is in no way limitative and should be read with reference to the attached drawings on which.

DETAILED DESCRIPTION OF THE INVENTION

Figure 1:
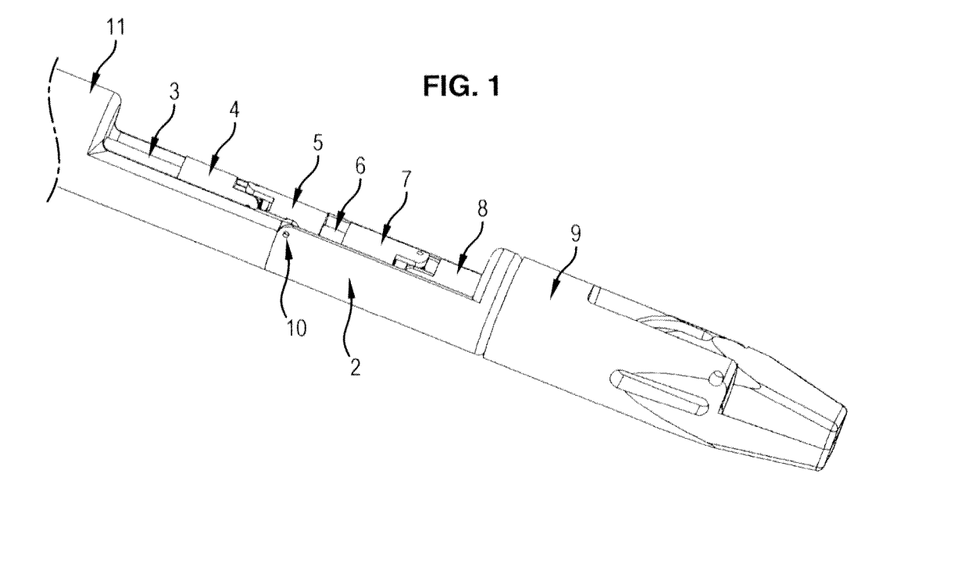
FIG. 1 is a side view of the distal end of a surgical instrument according to a first embodiment of the invention.
Figure 2:
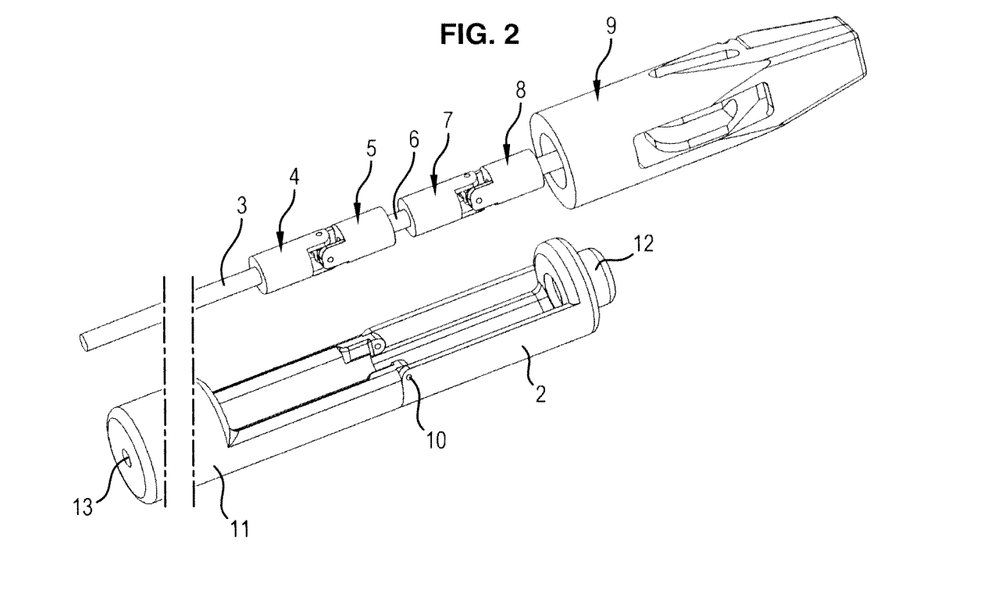
FIG. 2 is a two part view of the surgical instrument of FIG. 1.

In reference to FIGS. 1 and 2, we will describe a first embodiment of a surgical instrument according to the invention.

FIG. 1 illustrates the distal part of a surgical instrument 1 according to a first embodiment of the invention. The surgical instrument 1 comprises an elongated arm 11, here in a cylindrical revolution shape according to a longitudinal axis (not shown). The elongated arm is hollow and has, on a distal part, an opening on a semi-circumference terminating longitudinally via linking means comprising an axis 10 substantially orthogonal to the longitudinal axis of the elongated arm 11 and extending according to a diameter of a section of said elongated arm 11. These linking means connect the elongated arm to a distal end 2 comprising, in this respect, complementary linking means. This forms a pivot joint between the elongated arm 11 and the distal and 2. The distal end 2 here is hollow, cylindrical in revolution in shape about an axis and open on a semi-circumference approximately over the entire length of the distal end 2, except at the level of an end face 12. The section of the distal end 2 is almost identical to that of the elongated arm 11. Accordingly, in an unfolded position, as illustrated in FIGS. 1 and 2, the distal end 2 extends in the longitudinal extension of the elongated arm 11, the longitudinal axis of the elongated arm 11 coinciding with the axis of the distal end 2. The end face 12 comprises a section of a shaft extending in projection towards the exterior along the axis of the distal end 2. A distal tool 9, here a forceps, is mounted in rotation on the section of shaft of the end face 12, in an extension according to the axis of the distal end 2. At the level of a proximal end, the elongated arm 11 comprises an end face comprising an axial bore 13, the longitudinal axis of the elongated arm 11.

Mounted substantially coaxially with elongated arm 11, the surgical instrument 1 according to the invention comprises a drive shaft 3 which extends in the elongated arm 11 from the bore 13 to the distal tool 9 with which it is solid to be able to drive it in a rotation movement about its axis. The drive shaft 3 here is free to turn according to its axis and slide according to a translation movement relative to the elongated arm 11 axis. The drive shaft 3, comprises, at its distal end, means forming a universal joint 4, 5, 6, 7 and 8 which extend, as shown in FIG. 1, into the openings made on a semi-circumference of the distal end 2 and of the elongated arm 11. The universal joint is thus facing the pivot joint, that is it is arranged to accompany the rotational movement of the pivot joint.

Here, in the embodiment of the invention described, the means forming universal joint comprise a first Cardan joint 4, 5 mounted in series with a second Cardan joint 7, 8 by a portion 6 of the drive shaft. In the present text as in conventional terms, a Cardan joint refers to a mechanical linking system comprising two end elements mounted on either side of a central element, where each end element is mounted in a pivot joint with the central element. In addition, the axes of the two pivot joints between the central element and the two end elements respectively are perpendicular (that is, orthogonal and secant) and therefore join at the same point, enabling transmission of angular rotation movement between two shafts extending respectively from the end elements.

In the example presented in FIGS. 1 and 2, the Cardan joints comprise a central piece in the form of a brace, the branches of the brace forming axes on which the end pieces 4, 5 and 7, 8 are mounted in a pivot joint.

The function fulfilled by the distal tool 9 is controlled by a cable which extends inside the drive shaft 3 which is hollow for this purpose. The cable is made of resistant metal but still remains sufficiently flexible to follow the movement of the distal end 2 when the pivot joint is used about the axis 10.

Figure 3A:
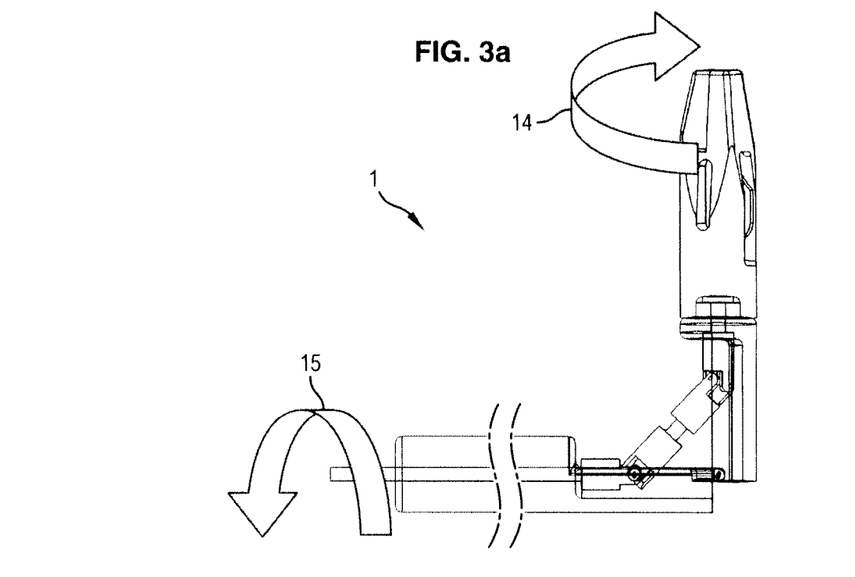
FIGS. 3a and 3b are side views of the surgical instrument of FIG. 1, the distal end being in a fully folded position and in a straight position respectively.
Figure 3B:
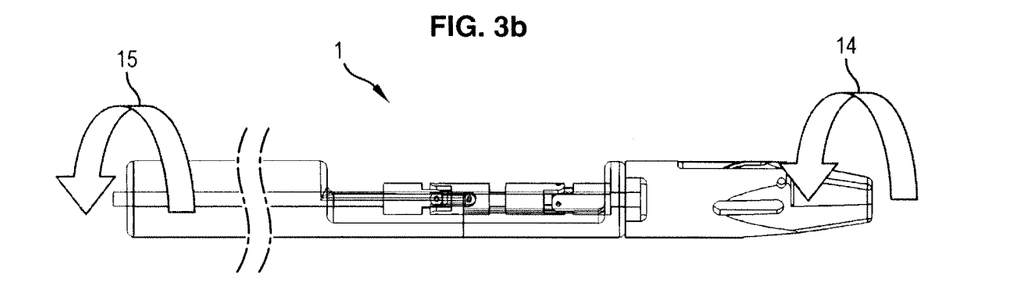

In reference to FIGS. 3a and 3b, a brief description follows of the functioning of the surgical instrument 1 according to the invention. FIG. 3a illustrates the folded position at around 90°, while FIG. 3b illustrates the unfolded position. In both cases, rotation movement 15 applied to the proximal end of the drive shaft causes a rotation movement 14 of the distal tool 9. A perfect transmission of his rotation movement is ensured by the means forming a universal joint, and this being irrespective of the degree of folding of the distal end 2 turning about the axis 10 of the pivot joint. A transition from the folded position to the unfolded position (or between two different folded positions) occurs via translation movement of the drive shaft 3 according to its axis. When the proximal end of the drive shaft is shifted according to this translation movement, an operator controls the orientation of the distal tool 9. This does away with the presence of cables to complete this orientation. In fact, this translation movement modifies the distance between the axis 10 of the pivot joint between the elongated arm 1 and the distal end 2 and orthogonal projection of any point of the distal tool 9 on the axis of the elongated arm 11. The rigidity of the distal end 11 causes a rotation movement about the axis 10 to produce a folded position (or unfolded), the drive shaft following the movement as a result of the means forming a universal joint.

Figure 4:
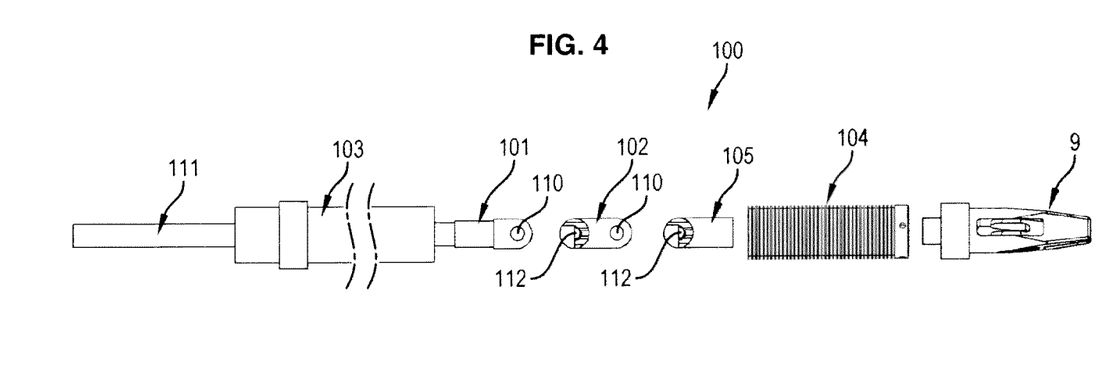
FIG. 4 is an exploded side view of a surgical instrument according to a second embodiment of the invention.
Figure 5:
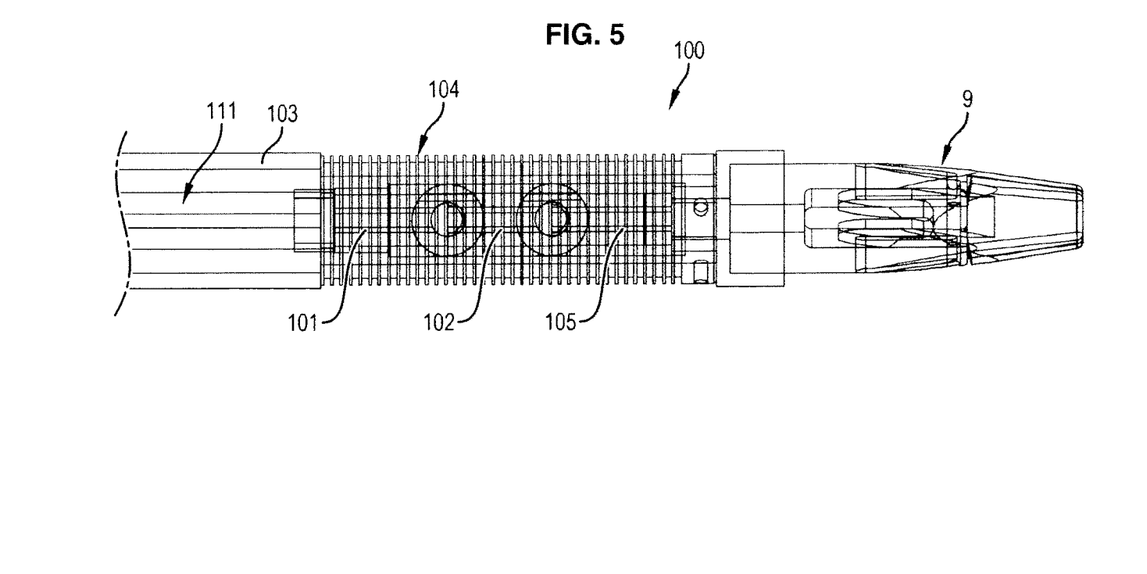
FIG. 5 is a side view of the distal end of the surgical instrument of FIG. 4.

In reference to FIGS. 4 and 5, a second embodiment of a surgical instrument 100 according to the invention will now be described. The surgical instrument 100 according to the invention comprises an elongated arm 111, here cylindrical in revolution in shape according to a longitudinal axis (not shown). The elongated arm 111 distally comprises a base linking element 101 comprising an axis 110 substantially perpendicular to the longitudinal axis of the elongated arm 111. The elongated arm 111 further comprises a second linking element 102 comprising a bore 112 at a proximal end and an axis 110 similar to the axis 110 of the base linking element 101 and situated at a distal end of the second linking element 102. The second linking element 102 is mounted in rotation on the base linking element 101 by cooperation of the axis 110 of the base linking element 101 and the bore 112 of the second linking element 102, thus forming a pivot joint. The elongated arm 111 further comprises a third linking element 105 comprising, at a proximal end, a bore 112 similar to the bore 112 of the second linking element 102. Similarly, the third linking element 105 is mounted in rotation on the second linking element 102 by cooperation of the axis 110 of the second linking element 102 with the bore of the third linking element 105, thus forming a second pivot joint. This third linking element 105 forms the distal end of the elongated arm 111. Mounted on a distal end of the third linking element is the distal tool 9, here a forceps, in an extension of the third linking element 105. The latter is mounted in rotation about a longitudinal axis of the third linking element 105 on the latter. As a variant embodiment, several linking elements 102 can be mounted in series between the base linking element 101 and the third linking element 105 bearing the distal tool 9. Accordingly, the distal tool 9 is mounted in rotation on and in the extension of the distal end of the elongated arm 111. The distal end of the elongated arm 111 formed by the third linking element 105 is mounted according to a pivot joint on the latter.

Figure 6A:
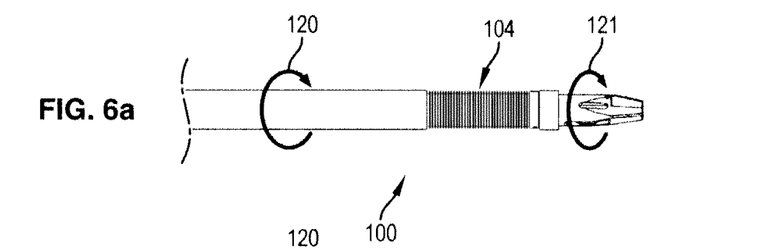
FIGS. 6a and 6b are side views similar to FIGS. 3a and 3b applied to the surgical instrument of FIG. 1.

Mounted substantially coaxially with the elongated arm 111, the surgical instrument 100 according to the invention comprises a drive shaft 103 which extends about the elongated arm 111 from substantially a proximal end of said elongated arm 111 and substantially a proximal part of the base linking element 101. A drive sleeve 104 is mounted firmly on a distal end of the drive shaft 103 in the extension of the latter. The drive sleeve 104 is mounted on the distal tool 9 so as to drive it in rotation movement about its axis. The drive sleeve 104 is arranged to extend about the base linking element 101, of the second linking element(s) 102 and of the third linking element 105, once mounted, as illustrated in FIG. 5. The drive shaft 103, and consequently the sleeve 104, is free to turn according to its axis relative to the elongated arm 111. The drive sleeve 104 forms means forming a universal joint. The drive sleeve 104 is rigid with regard to torsion stress according to the longitudinal axis, and is flexible and deformable elastically with regards to torsion stress according to any axis perpendicular to the longitudinal axis. Torsion according to an axis corresponds to the twisting about such axis produced by the action of two opposing couples acting in parallel planes. In the embodiment of FIGS. 4 and 5, the drive sleeve comprises bellows which is rigid with regard to torsion stress according to the longitudinal axis, so as to transmit the rotation movement about this axis of the drive shaft 103 to the distal tool 9, and which is flexible and deformable elastically with regard to torsion stress according to any axis perpendicular to the longitudinal axis, so as to deform easily when pivot joints are used between the base linking element 101 and second 102 and third 105 linking elements (cf. FIGS. 6a and 6b). The bellows may for instance be metallic. Any other adapted material can be used to make said bellows.

Figure 7A:
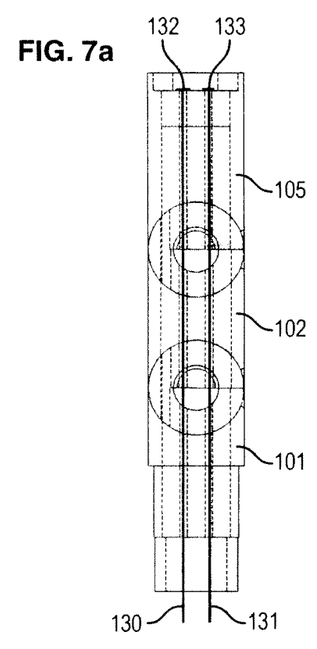
FIGS. 7a and 7b are cross section views of the driving mechanism of the pivot joint of the distal end of the surgical instrument of FIG. 4, in a fully folded position and in a straight position respectively.
Figure 7B:
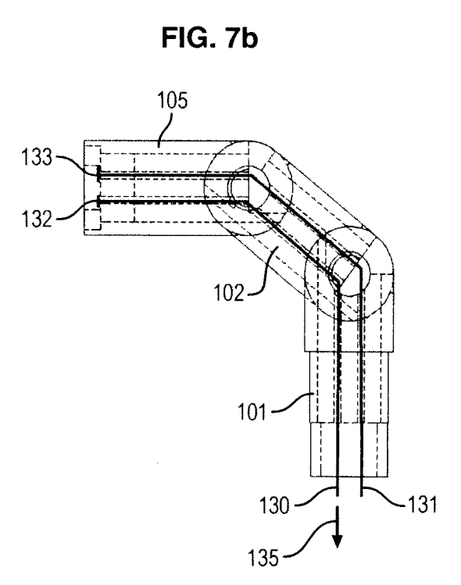

The function fulfilled by the distal tool 9 is controlled by a cable which extends inside the elongated arm 111 which is hollow, for this purpose. The cable is made of resistant metal but still remains sufficiently flexible to follow movement of the distal end when pivot joints are used about axes 110. Similarly, using pivot joints between the base linking element 101 and second 102 and third 105 linking elements is achieved by means of two cables 130 and 131 (cf. FIGS. 7a and 7b) extending inside the elongated arm 111 substantially parallel relative to one another and relative to the longitudinal axis of the elongated arm 111, on the one hand, and on the other hand, spaced apart on either side of said longitudinal axis. Each cable 130 (resp. 131) comprises a distal end 132 (resp. 133) securely fastened with the third linking element 105. Traction force 135 on one of the cables utilises the abovementioned pivot joints as is illustrated in FIG. 7b. These different cables can be enclosed by a sheath which protects them, but which also allows the length of the cable or cables placed according to the principal axis of insertion to be independent of the flexion of the surgical instrument and force these cables to follow curvature of the principal axis. This avoids for instance that pulling cable actuating distal tool 9 creates forces on the surrounding structure when distal tool 9 is pivoted with respect to elongated arm 207.

Figure 6B:
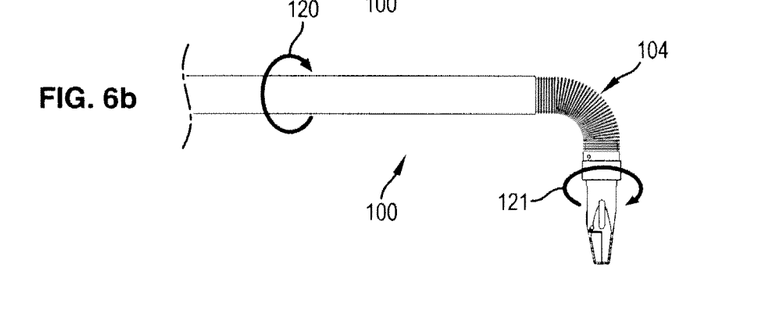

Operation of the surgical instrument 100 according to the invention will now be described in brief. FIG. 6b (7b) illustrates the folded position at around 90°, while FIG. 6a (7a) illustrates the unfolded position. In both cases, a rotation movement 120 applied to the proximal end of the drive shaft causes rotation movement 121 of the distal tool 9. Perfect transmission of this rotation movement is ensured by the means forming a universal joint (drive sleeve 104) and, this being irrespective of the degree of folding of the distal end turning about axes 110 of the pivot joints. Transition from the folded position to the unfolded position (or between two different folded positions) occurs via translation movement 135 of one of the cables 130, 131 according to its axis. An operator controls orientation of the distal tool 9 by moving one of these cables according to this translation movement.

In reference to FIGS. 8 and 9, a third embodiment of a surgical instrument 200 according to the invention will now be described. The surgical instrument 200 according to the invention comprises an elongated arm 207, here cylindrical in revolution in shape according to a longitudinal axis (not shown). The elongated arm 207 is hollow and distally comprises a base linking element 201 hollow, comprising two lugs extending in the extension of the elongated arm 207 and opposite one another to define an axis 210 substantially perpendicular to the longitudinal axis of the elongated arm 207. The elongated arm 207 further comprises second hollow linking elements 202, 203 (also called intermediate linking elements), comprising two lugs extending in the extension of said second linking elements 202, 203 and opposite one another to define an axis 210 similar to the axis 210 of the base linking element 201 and located at a distal end of the second linking elements 202, 203. The second linking element 202 is mounted in rotation relative to the axis 210 on the base linking element 201, thus forming a pivot joint. Similarly, the second linking elements 202 and 203 are mounted in rotation relative to their mutual axis 210, thus forming a second pivot joint. The elongated arm 207 further comprises a third hollow linking element 204 (also called and linking element). Similarly, the third linking element 204 is mounted in rotation relative to the axis 210 on the second linking element 203, thus forming a third pivot joint. This third linking element 204 forms the distal end of the elongated arm 207.

Mounted on a distal end of the third linking element 204 is the distal tool 9, here a forceps, in an extension of the third linking element 204. The distal tool 9 is mounted in rotation about a longitudinal axis of the third linking element 204 on the latter. As a variant embodiment, more than two linking elements 202, 203 can be mounted in series between the base linking element 201 and the third linking element 204 bearing the distal tool 9. Accordingly, the distal tool 9 is mounted in rotation on and in the extension of the distal end of the elongated arm 207. The distal end of the elongated arm 207 formed by the third linking element 204 is mounted according to a pivot joint on the latter.

As a variant embodiment, the third linking element 204 is mounted directly in series on the base linking element 201. As another variant embodiment, a single second linking element 202 is mounted in series between the third linking element 204 and the base linking element 201.

All the linking elements (201, 202, 203, 204) are segmented elements which, when mounted in series, fulfill the pivot function. This assembly of linking elements (201, 202, 203, 204) can be similar to a set of hollow vertebrae of substantially cylindrical form, each of the vertebrae being mounted with the preceding vertebra with a pivot joint according to a pivot axis 210 perpendicular to the longitudinal axis of the elongated arm 207. Such pivot joint is also referred as a limited pivot joint or wedged pivot joint, as the angular amplitude of the pivot is structurally restricted by the form of the linking elements. All the axes of the pivot joints 210 are parallel such that the total angle of flexion is the sum of the angles of rotation between each pair of vertebrae. The series of the limited pivot joints produces an accumulative pivot with respect to the whole body, which corresponds to the overall pivot joint.

According to a preferred embodiment, the hollow vertebrae have a substantially cylindrical form. They can be assembled with others like puzzle pieces, by having one piece slide relative to the other according to the axis of the pivot 210. Accordingly it is not necessary to provide a rod to physically form the pivot joint which is in reality ensured by cooperation of the lugs of each vertebra with a complementary form arranged on the following vertebra, this complementary form for example being a notch made from the edge of the cylinder forming the vertebra. Such an arrangement considerably simplifies assembling of the assembly. In addition, such a configuration also has the advantage of forming a pivot joint without introducing dents or additional structure in the internal wall or in the external wall of the vertebra, ensuring no loss of room inside the vertebra on the one hand, and on the other hand ensuring a smooth surgical instrument without an element which might impede its displacement in the insertion trocar of the surgical instrument. It should be noted that the vertebrae are kept in a nested position in one another by any means, but will preferably be held by the actuating cables of the pivot joints passing through the vertebrae, and/or the elements placed inside the vertebrae and ensuring this position is kept especially by overlapping of the pieces. Other methods of coupling the vertebrae are feasible, for example by arranging a cavity on the surface of the vertebra, this cavity cooperating with an embossing extending from the inner surface of the lug, enabling fixing via clipping for example. According to a preferred embodiment, though not necessary, all the vertebrae are identical.

Ensuring the pivot function by a net of vertebrae such as described hereinabove has numerous advantages. First, as already pointed out, specific assembling (by nesting/puzzle, and even by clipping) maintains a large enough inner space for placing the other mechanical functions necessary for the surgical instrument. In addition, the proposed arrangement uses small-sized pieces and guarantees an outer diameter of the surgical instrument of the order of 5 mm, ensuring considerable angular amplitude of the pivot and satisfactory rigidity of the assembly for manipulation of the surgical instrument. In fact, using a series of successive vertebrae easily produces the angular amplitude generally used of the order of 90°, since each pivot between two successive vertebrae permits angular amplitude of at least 20° (corresponding to what qualifies as a limited pivot joint). Also, the proposed arrangement ensures the required rigidity for good manipulation of the surgical instrument, especially torsional rigidity according to the axes orthogonal to the axis of the overall pivot, this being due especially to the full cylindrical form of the vertebrae and to their particular coupling. In addition, the fact that the axes of the pivots 210 are perpendicular to the longitudinal axis of the elongated arm 207 allows the lugs of the vertebrae to be arranged in the body of the cylinder according to a diametrical axis, preventing them from projecting relative to the outer wall of said cylinder.

Figure 8:
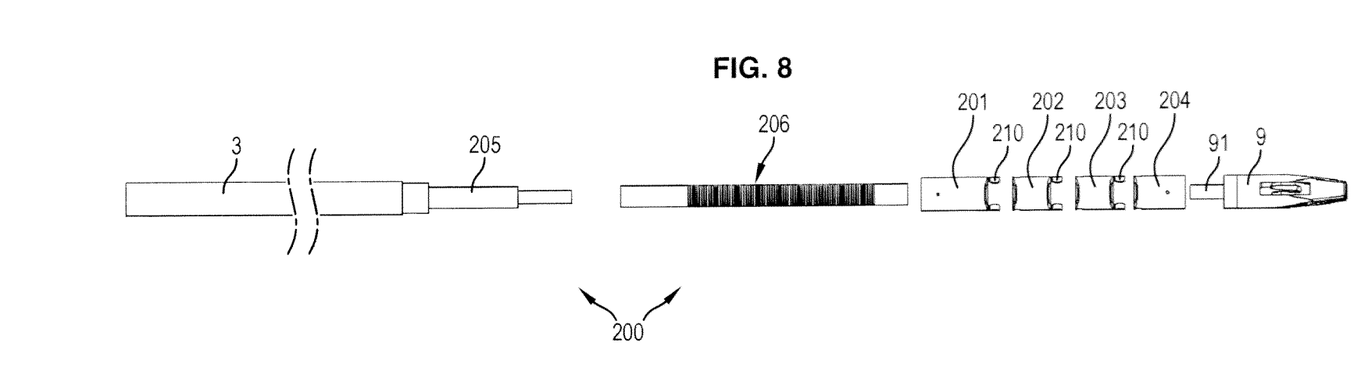
FIG. 8 is an exploded view of a surgical instrument according to a third embodiment of the invention.
Figure 9:
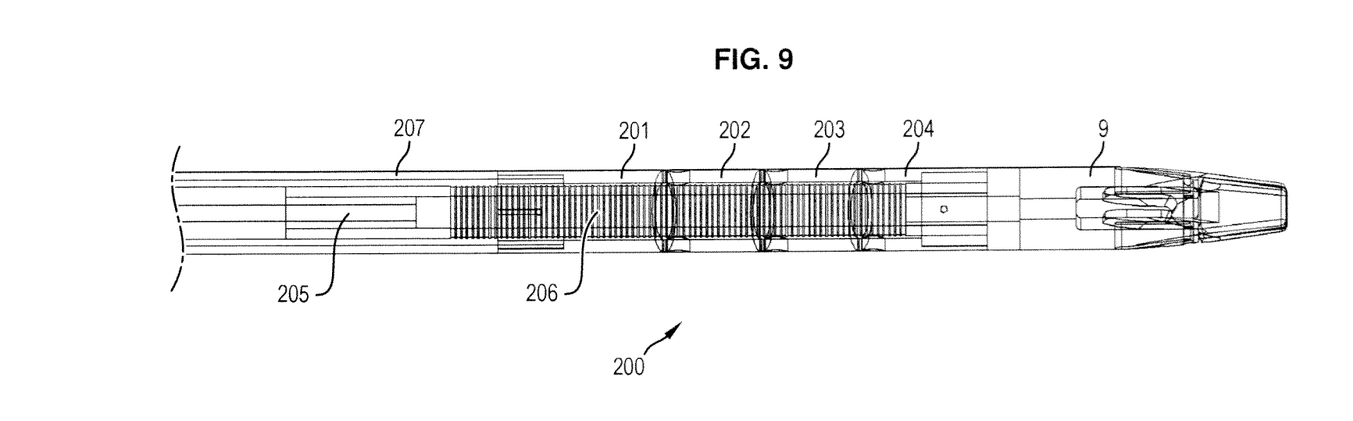
FIG. 9 is a cross section of the distal end of the surgical instrument of FIG. 8.
Figure 10A:
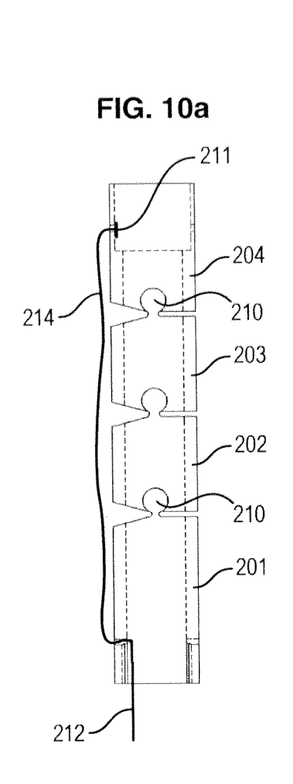
FIGS. 10a and 10b are mechanical illustrations of the drive of the pivot joint of the distal end of the surgical instrument of FIG. 8, in a straight position and in a fully folded position respectively where only the active wires are shown.
Figure 10B:
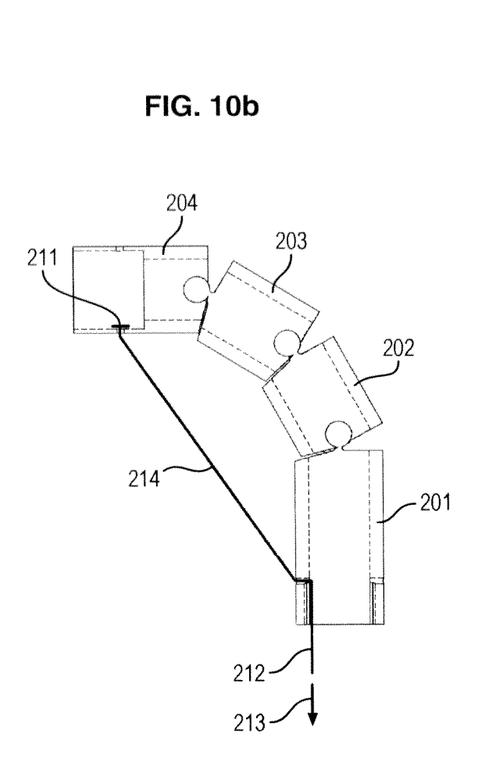

Mounted substantially coaxially with the elongated arm 207, the surgical instrument 200 according to the embodiment presented in FIGS. 8 to 10 comprises a drive shaft 3 which extends in the elongated arm 207 from substantially a proximal end of said elongated arm 207 and substantially a proximal part of the base linking element 201. A drive sleeve 206 is mounted solid on a distal end of the drive shaft 3 in the extension of the latter. The drive sleeve 206 is securely fastened with the distal tool 9 so as to drive it in rotation movement about its axis. The drive sleeve 206 is arranged to extend within the base linking element 201, the second linking elements 202, 203 and the third linking element 204, once mounted, as illustrated in FIG. 9. The drive shaft 3, and consequently the sleeve 206, is free to turn according to its axis relative to the elongated arm 207. The drive sleeve 206 forms means forming a universal joint. The flexible drive sleeve is rigid with regard to torsion stress according to the longitudinal axis, and is flexible and deformable elastically with regard to torsion stress according to any axis perpendicular to the longitudinal axis. In the embodiment of FIGS. 8 and 9, the drive sleeve comprises bellows which are rigid with regard to torsion stress according to the longitudinal axis, so a to transmit rotation movement about this axis of the drive shaft 3 to the distal tool 9, and flexible and deformable elastically with regard to torsion stress according to any axis perpendicular to the longitudinal axis, so as to deform easily when pivot joints are used between the base linking element 201 and second 202, 203 and third 204 linking elements. The bellows may for instance be metallic. Any other adapted material can be used to make said bellows.

The function fulfilled by the distal tool 9 is controlled by a cable 205 which extends inside the drive shaft 3 which is hollow, for this purpose. The cable 205 is made of resistant metal but still remains sufficiently flexible to follow the movement of the distal end when pivot joints are used about axes 210. Similarly, using pivot joints between the base linking element 201 and second 202, 203 and third 204 linking elements is achieved by means of a cable 212 (cf. FIGS. 10*a* and 10*b*) extending inside the elongated arm 207 from the proximal part of the base linking element 201. The cable 212 comprises a distal end 211 securely fastened with the third linking element 204. Part 214 of the cable extends outside the elongated arm 207, opposite the second linking elements 202, 203. Traction force 213 on the cable utilises the above pivot joints, as is illustrated in FIG. 10*b*. As a variant, a second cable can be used, located diametrically opposite the cable 212. As another variant, the part 214 of the cable extends inside the second linking elements (if a second cable is used, the latter can also extend inside the second linking elements). These different cables can be enclosed by a sheath which protects them, but which also allows the length of the cable or cables placed according to the principal axis of insertion to be independent of the flexion of the surgical instrument and force these cables to follow curvature of the principal axis. This avoids for instance that pulling cable actuating distal tool 9 creates forces on the surrounding structure when distal tool 9 is pivoted with respect to elongated arm 207.

The function of the surgical instrument 200 according to the invention will now be described in brief. FIG. 10*b* illustrates the folded position at around 90°, while FIG. 10*a* illustrates the unfolded position. In both cases, rotation movement applied to the proximal end of the drive shaft causes rotation movement of the distal tool 9. Perfect transmission of this rotation movement is ensured by the means forming a universal joint (drive sleeve 206) and, this being irrespective of the degree of folding of the distal end turning about axes 210 of the pivot joints. Transition from the folded position to the unfolded position (or else between two different folded positions) is done via translation movement 213 of the cable 212 according to its axis. An operator controls the orientation of the distal tool 9 by moving this cable according to this translation movement.

In reference to FIGS. 11 to 16, a fourth embodiment of a surgical instrument 300 according to the invention will now be described. The surgical instrument 300 according to the invention comprises an elongated arm 307 having a form similar to the elongated arm 207 of the surgical instrument 200 according to the third embodiment of the invention. Accordingly, the elongated arm 307 comprises one or more linking elements making up the pivot function, where the set of linking elements can be similar to a set of hollow vertebrae, each of the vertebrae being mounted according to an axis pivot joint perpendicular to the axis of the elongated arm with the preceding vertebra.

Figure 11:
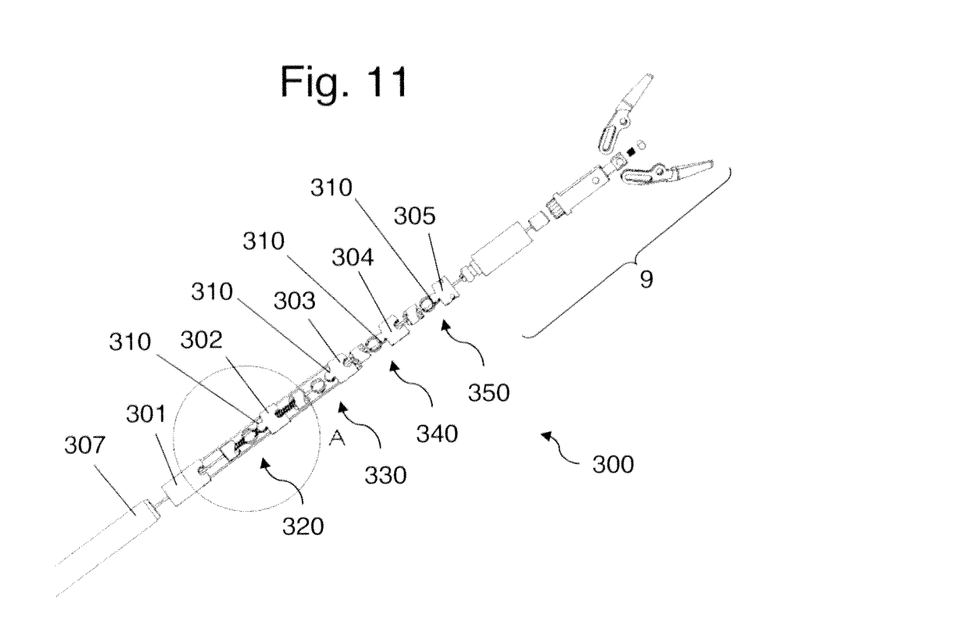
FIG. 11 is an exploded perspective view of a surgical instrument according to a fourth embodiment of the invention.

More precisely, in the fourth embodiment presented, the elongated arm 307 comprises five linking elements (301, 302, 303, 304, 305) forming the pivot joint (also called overall pivot joint). The elongated arm 307 is hollow and distally comprises a hollow base linking element 301, comprising one set of pivot lugs (female side only) extending in the direction of the elongated arm 307 and opposite one another to define an axis 310 substantially perpendicular to the longitudinal axis of the elongated arm 307. The elongated arm 307 further comprises hollow intermediate linking elements (302, 303, 304), comprising two lugs extending in the extension of said intermediate linking elements (302, 303, 304) and opposite one another to enable rotation about an axis parallel to the axis 310 of the base linking element 301 and located at a distal end of the intermediate linking elements (302, 303, 304). The intermediate linking element 302 is mounted in rotation relative to the axis 310 on the base linking element 301, thus forming a first limited pivot joint (also called wedged pivot joint, as the form of the linking elements naturally restrict the amplitude of the pivot). Similarly, the intermediate linking elements (302, 303, 304) are mounted in mutual rotation relative to the axis 310, thus forming a second and third limited pivot joint. The elongated arm 307 further comprises a hollow end linking element 305. Similarly, the end linking element 305 is mounted in rotation relative to the axis 310 on the final intermediate linking element 304, thus forming a fourth limited pivot joint. This end linking element 305 forms the distal and of the elongated arm 307. The series of the limited pivot joints produces an accumulative pivot with respect to the whole body, which corresponds to the overall pivot joint. All the axes of the pivot joints 310 are parallel such that the total angle of flexion is the sum of the angles of rotation between each pair of linking elements.

In addition, the vertebrae are pierced to allow two cables (312, 314) placed on either side of the axis of the pivot 310 to slide. The cables (312, 314) are attached to the final vertebra and slide in the openings of the others, which allow all the pivots to be actuated after mounting and therefore flexes by pulling on one or the other of the two cables (312, 314).

Mounted substantially coaxially with the elongated arm 307, the surgical instrument 300 comprises a drive shaft 3 which extends in the elongated arm 307 from substantially a proximal end of said elongated arm 307 to substantially a proximal part of the base linking element 301. The drive shaft 3 comprises, at its distal end, means forming a universal joint which extend in the cavity formed by the different linking elements, these means forming a universal joint comprising at least one Cardan joint. The means forming a universal joint preferably comprise at least two Cardan joints. To maintain the full range of motion (longitudinal and radial rotation), the means forming a universal joint more preferably comprise as many Cardan joints as pivot axes 310 formed by the vertebrae (301, 302, 303, 304, 305). Accordingly, in the example presented in FIGS. 11 to 16, four Cardan joints (320, 330, 340, 350) are provided, respectively positioned at the level of the pivot axes 310 formed between the different linking elements (301, 302, 303, 304, 305), that is adjacent to the corresponding pivot joint. According to a preferred aspect of this embodiment, the axes of the two pivot joints defining each Cardan joint intersect with the pivot axis 310 at the level where it is positioned.

As pointed out earlier, a Cardan joint is a mechanical linking system comprising two end elements mounted on either side of a central element, where each end element is mounted in a pivot joint with the central element. In the embodiment presented in FIGS. 11 to 16, the pivot joints between the pieces forming the Cardan joint are made by a sliding guide of one surface on another. To achieve this, end pieces having at their end of the surfaces sliding on the surface of the central piece can be provided for example, these central and end pieces also comprising sliding guide means.

Figure 12:
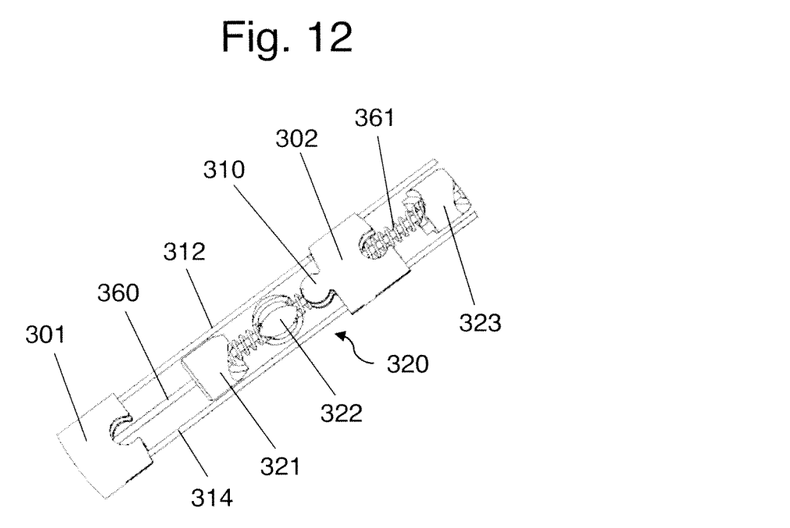
FIG. 12 is an enlarged view, in an exploded perspective view, of the portion referenced as A of the surgical instrument of FIG. 11.

Accordingly, as is evident from FIG. 12, the central piece 322 of the Cardan joint 320 is preferably a sphere in which two grooves are hollowed out in two perpendicular diametrical planes, preferably according to two diametrical circles. More preferably, each groove forms a circle around the sphere. The end pieces 321 and 323 have as such ends formed to be able to slide on the sphere 322, having hollow/concave surfaces with for example a semi-cylindrical or semi-spherical form complementary to the sphere 322. The contact surfaces at the ends of the end pieces 321 and 323 also preferably comprise a ridge in projection whereof, said ridge having a form corresponding to the geometry of the hollow grooves in the sphere 322, such that the ridge in projection serves as guide rail for sliding of the end pieces 321 and 323 on the central piece 322. The end pieces 321 and 323 also have a general cylinder form. In a preferred embodiment, two successive Cardan joint could have a common end piece (corresponding to the end piece positioned between the two spheres of the two Cardan joints) having the form of a cylinder with at its two ends a hollow surface formed for sliding on the spheres.

In the present embodiment, shoulders preferably prevent the sliding according to the axis of the drive shaft 3 and the contact between the sliding surfaces is maintained by external pressure, due especially to the mechanical assembling of the different pieces. As pointed out earlier, the spheres are preferably placed such that their centre belongs to the pivot axis of the vertebrae, such that the axes of the pivot joint made by the contact surfaces intersect the pivot axis of the vertebrae. All the pieces forming the Cardan joints are small enough to be nestled inside the vertebrae. The outer diameter of the cylinders forming the end pieces of the Cardan joints is preferably adjusted to the inner diameter of the vertebrae so that the cylinders can slide inside the vertebrae, thus facilitating assembling of the assembly, since the cylinders and spheres forming the Cardan joints can be inserted and slide inside the vertebrae according to the longitudinal axis of the elongated arm 307.

Assembling such a set of Cardan joints therefore consists of inserting in the vertebrae (301, 302, 303, 304, 305) and stacking between them a succession of cylindrical elements and spherical elements, respectively forming the end elements and central elements of the Cardan joints (320, 330, 340, 350). Accordingly, the ridge in projection of a cylinder is inserted into the groove of the sphere in which the ridge in projection of the preceding cylinder is not inserted, the ridges in projection of two consecutive cylinders in contact with the sphere connecting it therefore being orthogonal. It is ensured that the centre of the spheres is positioned according to the pivot axis of the corresponding vertebrae. The assembly is then blocked in translation by the stacked axis corresponding to the longitudinal axis of the elongated arm 307, by a screw system, for example. Transmission of the intrinsic rotation of the distal part is then possible between the most proximal cylinder and the most distal cylinder by relative shifts of the cylinders and of these spheres which respect Cardan kinematics. Advantageously, transmission can overall remain homokinetic if, for each intermediate cylinder, the ridges in projection of the ends are machined orthogonally relative to one another, and if the number of Cardan joints is even.

As for the others embodiments, a distal tool 9, for example a forceps, is mounted on a distal end of the end linking element 305, in its extension. The distal tool 9 is mounted in rotation about a longitudinal axis of the element end linking element 305 on the latter. This distal tool 9 is preferably actuated by a cable extending inside the elongated arm 307. More preferably, the cylindrical and spherical pieces forming the transmission by Cardan joints are pierced by throughholes according to the principal axis of the instrument when the latter is not flexed. These different holes made in the pieces of the Cardan joints allow a flexible mechanical cable 360 to pass through for transmission of traction force to actuate the distal tool 9 placed at the distal end of the instrument, or of electric cables (not shown) for transmission of a signal, a command or a monopolar and/or bipolar current. This or these cables are preferably enclosed by a sheath 361 which on the one hand protects this or these cables, but also the length of the cable or cables placed according to the principal axis of insertion is independent of the flexion of the surgical instrument and force these cables to follow curvature of the principal axis. This avoids for instance that pulling cable actuating distal tool 9 creates forces on the surrounding structure when distal tool 9 is pivoted with respect to elongated arm 207.

Figure 13:
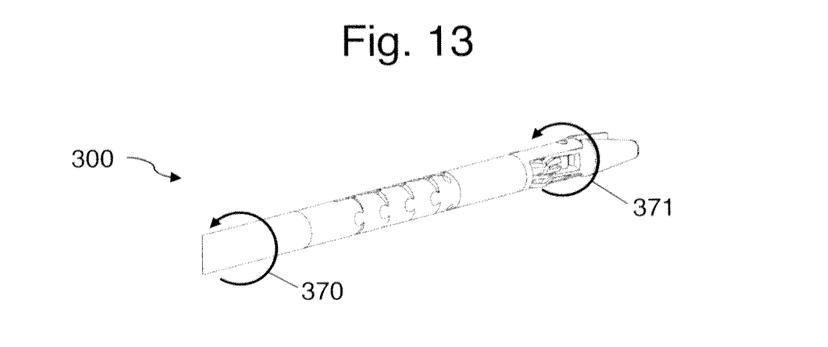
FIG. 13 is a perspective view of the surgical instrument of FIG. 11, the distal end being in a straight position.
Figure 14:
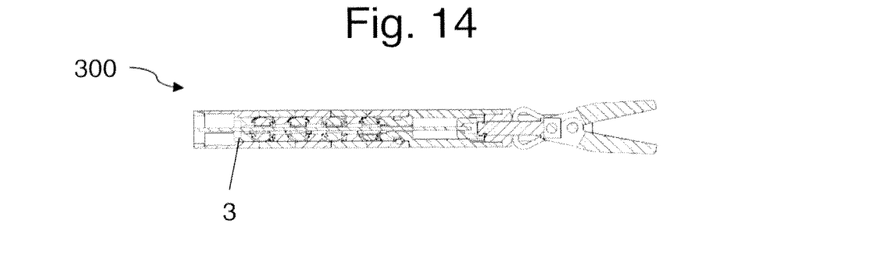
FIG. 14 is a cross sectioned view of the surgical instrument of FIG. 11, the distal end being in a straight position.
Figure 15:
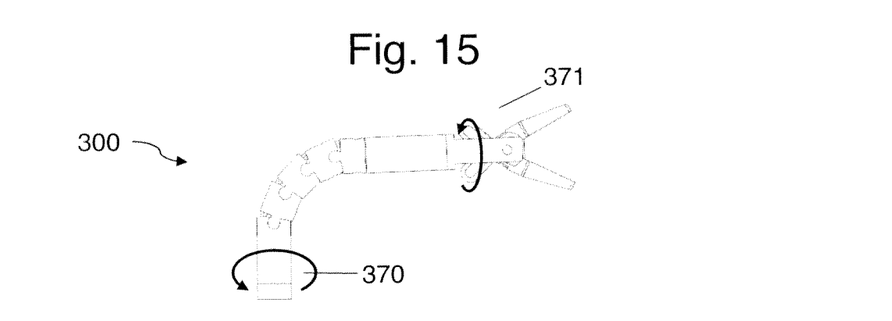
FIG. 15 is a perspective view of the surgical instrument of FIG. 11, the distal end being in a fully folded position.
Figure 16:
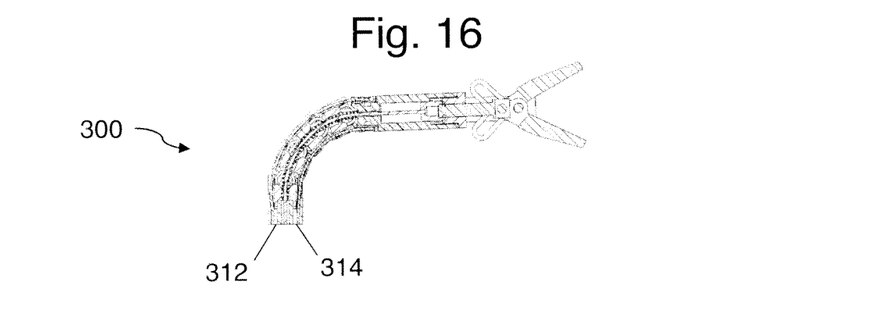
FIG. 16 is a cross sectioned view of the surgical instrument of FIG. 11, the distal end being in a fully folded position.

Operation of the surgical instrument 300 according to the invention will now be described. FIGS. 15 and 16 illustrate the folded position at 90°, while FIGS. 13 and 14 illustrate the unfolded position. In both cases, a rotation movement 370 applied to the proximal end of the drive shaft causes rotation movement 371 of the distal tool 9. Perfect transmission of this rotation movement is ensured by the means forming a universal joint (Cardan joints 320, 330, 340, 350) and, this being irrespective of the angular deflection of the distal end turning about axes 310 of the limited pivot joints. The transition of the folded position to the unfolded position (or between the two different folded positions) occurs via translation movement of one of the cables 312, 314 according to its axis. An operator controls the orientation of the distal tool 9 by moving one of these cables according to this translation movement.

Controlling of the different cables used in the described surgical instrument, for example the actuating cables of the distal tool and/or the actuating cables of the pivot joint, could be done manually by the user, or by means of one or more motors automating operation of the surgical instrument. A motor can also be used to set the drive shaft in rotation about its longitudinal axis.

Figure 17:
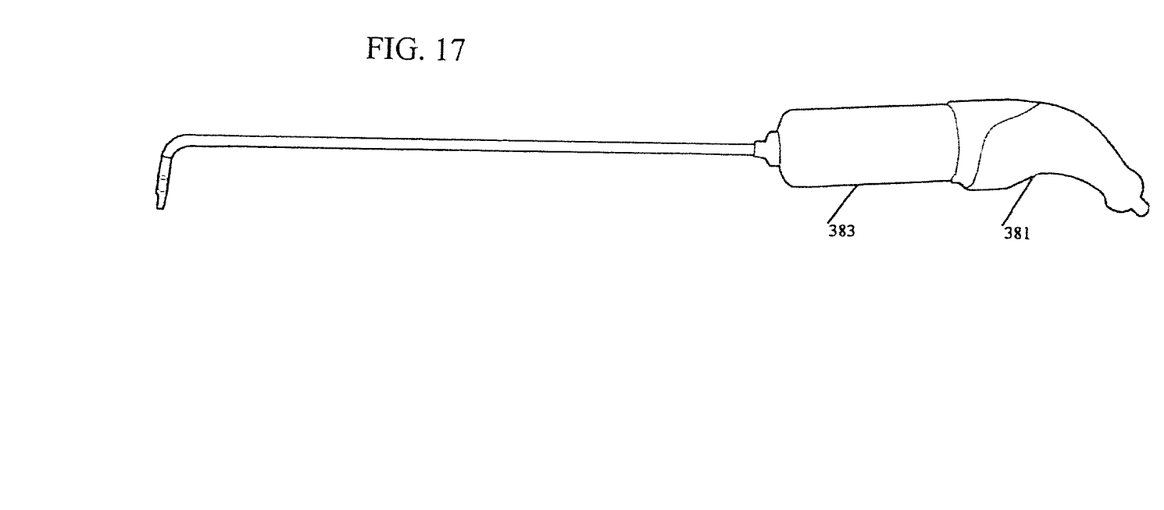
FIG. 17 is a view of the surgical instrument including its handle and transmission system.

FIG. 17 illustrates the surgical instrument including a handle 381 and transmission system 383.

The described surgical instrument distinguishes itself from existing instruments by having distal mobility in that the intrinsic rotation movement of the forceps is completely independent of the other movements (especially those which orient the axis of the forceps relative to the principal axis of the instrument) and transmitted directly via rotation movement carried out at the level of the proximal part.

This allows control of two movements of the distal part from two independent movements engendered at the level of the handle, which are orientation of the axis of the forceps due to rotation about an axis substantially orthogonal to the axis of insertion of the instrument and rotation about the axis of the forceps.

It is of course possible to make numerous modifications to the invention without departing from the scope thereof.

The invention claimed is:

1. A surgical instrument (1) comprising:
an elongated arm (11; 307) extending along a longitudinal axis and having a distal end (2; 305) coupled to said elongated arm via a pivot joint structure around an axis orthogonal to the longitudinal axis;
a drive shaft (3) coaxial with the elongated arm comprising a universal joint structure facing the pivot joint structure; and,
a distal tool (9) coupled to the drive shaft via the universal joint structure and rotationally coupled to the distal end of the elongated arm, such that the distal tool has two rotational degrees of freedom, distinct and independent of each other, one being around an axis perpendicular to the longitudinal axis of the elongated arm and the other being around an axis collinear to an own axis of the distal tool;
wherein the pivot joint structure comprises a plurality of linking elements mounted in series, with two adjacent linking elements including a limited pivot joint, and
the universal joint structure comprises a plurality of Cardan joints (320, 330, 340, 350), wherein there are an equal number of Cardan joints and limited pivot joints (310), wherein each said Cardan joint (320) comprises two end elements (321, 323) mounted on either side of a central element (322), each end element (321, 323) being mounted with a pivot joint on the central element (322) around pivot axes perpendicular to each other.

2. The surgical instrument of claim 1, wherein each linking element (301, 302, 303, 304, 305) is a hollow cylindrical element comprising two lugs extending towards the adjacent linking element, said lugs being opposite one another to define the limited pivot joint (310).

3. The surgical instrument of claim 2, wherein the limited pivot joint defined by the lugs of each linking element comprises an axis, the axes of all the limited pivot joints being parallel to one another.

4. The surgical instrument of claim 2, wherein the Cardan joints are nested inside the hollow cylindrical linking elements.

5. The surgical instrument of claim 1, wherein the universal joint structure comprises at least four Cardan joints (320, 330, 340, 350) and the elongated arm comprises at least five linking elements mounted in series to form the pivot joint with four limited pivot joints (310).

6. The surgical instrument of claim 1, wherein each Cardan joint (320, 330, 340, 350) is facing one of the limited pivot joints (310) formed by the linking elements (301, 302, 303, 304, 305) mounted in series, each Cardan joint (320, 330, 340, 350) comprising two pivot axes intersecting with a pivot axis of the corresponding limited pivot joint (310).

7. The surgical instrument of claim 1, wherein the pivot joints between each of the end elements (321, 323) and the central element (322) are made by a guided sliding of corresponding contact surfaces.

8. The surgical instrument of claim 7, wherein the central element (322) has the form of a sphere with two grooves hollowed in two perpendicular diametrical planes, and in that the end elements (321, 323) have ends with a concave surface formed to be able to slide on the sphere (322).

9. The surgical instrument of claim 8, wherein the concave surfaces of the end elements (321, 323) further comprise a ridge in projection with a shape complementary to the grooves of the sphere (322), such that the ridges in projection serve as guide rail for sliding of the end elements (321, 323) on the central element (322).

10. The surgical instrument of claim 7, wherein the end elements (321, 323) and the central element (322) of the Cardan joint comprise a through-hole along the longitudinal axis, one or more cables extending in the elongated arm via the through-hole.

11. The surgical instrument of claim 1, wherein an actuating cable (360) of the distal tool (9) extends within the elongated arm via the through-hole, said actuating cable (360) being surrounded by a sheath (361).

12. The instrument of claim 1, wherein the drive shaft is further slidingly mounted through a translation relative to the elongated arm along the longitudinal axis, the universal joint structure comprising two Cardan joints (4, 5; 7, 8) mounted in series.

13. The surgical instrument of claim 1, wherein the elongated arm is hollow and at least partially encloses the drive shaft.

14. The surgical instrument of claim 1, wherein it further comprises:
a handle; and,
a transmission system,
the handle being connected to the proximal end of the elongated arm, the movements according to the two degrees of freedom being connected by the transmission system to two independent movements produced at the handle.

15. The surgical instrument of claim 14, further being arranged such that the amplitude of rotation of the tool about its own axis is not structurally limited by the transmission system.

16. The surgical instrument of claim 1, wherein the limited pivot joint defined between two adjacent linking elements comprises an axis, the axes of all the limited pivot joints being parallel to one another.

17. The surgical instrument of claim 1, wherein each linking element is a hollow cylindrical element comprising two lugs extending towards an adjacent linking element, wherein the lugs of said linking element are configured to cooperate with a complementary form arranged on the adjacent linking element in order to form the limited pivot joint.

18. The surgical instrument of claim 17, wherein the linking elements are maintained in a nested position relative to one another by actuating cables passing through holes in the linking elements.

19. The surgical instrument of claim 18, wherein the actuating cables are for actuating the pivot joint.

* * * * *